United States Patent [19]

Taube

[11] Patent Number: 5,388,575

[45] Date of Patent: Feb. 14, 1995

[54] ADAPTIVE CONTROLLER FOR AUTOMATIC VENTILATORS

[76] Inventor: John C. Taube, 1531 Hanover St., Raleigh, N.C. 27608

[21] Appl. No.: 950,897

[22] Filed: Sep. 25, 1992

[51] Int. Cl.$^6$ ............................................. A61M 16/00
[52] U.S. Cl. ........................... 128/204.23; 128/203.14; 128/716
[58] Field of Search ................... 128/204.23, 713–716, 128/204.21, 203.14

[56] References Cited

U.S. PATENT DOCUMENTS

| | | | |
|---|---|---|---|
| 2,414,747 | 1/1947 | Kirschbaum . | |
| 3,734,091 | 5/1973 | Taplin | 128/204.23 |
| 4,326,513 | 4/1982 | Schulz | 128/203.14 |
| 4,584,996 | 4/1986 | Blum | 128/204.21 |
| 4,665,911 | 5/1987 | Williams | 128/204.21 |
| 4,889,116 | 12/1989 | Taube | 128/204.23 |
| 5,003,985 | 4/1991 | White | 128/716 |
| 5,103,814 | 4/1992 | Maher | 128/204.18 |
| 5,178,151 | 1/1993 | Sackner | 128/672 |

OTHER PUBLICATIONS

Diane Blodgett, *Manual of Respiratory Care Procedures* (Philadelphia:Lippencott, 1987) pp. 204–205.

*Primary Examiner*—Edgar S. Burr
*Assistant Examiner*—Eric P. Raciti
*Attorney, Agent, or Firm*—John G. Mills & Associates

[57] ABSTRACT

An automatic controller utilizes a pulse oximeter signal to regulate the oxygen mixture output, peak expiratory end pressure, and inspiratory ventilation time from a positive pressure respiratory assist ventilator. The pulse oximeter senses a patient's hemoglobin saturation and pulse rate by an optical sensor to develop a signal which is used by calculator to determine the patient's corresponding partial pressure of arterial blood. The calculated partial pressure of arterial blood is then used by the calculator in determining the level of inspired oxygen, peak expiratory end pressure, and inspiratory ventilation time provided to the patient. The calculator generates a signal to control the level of inspired oxygen, expiratory end pressure, and inspiratory ventilation time output from a positive pressure respiratory assist ventilator. The level of inspired oxygen, peak expiratory end pressure, and inspiratory ventilation time provided from the ventilator to the patient is varied to maintain a desired predetermined partial pressure of arterial oxygen.

1 Claim, 3 Drawing Sheets

ADAPTIVE CONTROLLER FOR AUTOMATIC VENTILATORS

FIELD OF INVENTION

This invention relates to positive pressure ventilation systems and more particularly to automatic controls for the same.

BACKGROUND OF INVENTION

Devices for controlling oxygen content of blood by controlling breathing parameters such as inspiratory time, peak expiratory end pressure, and expired oxygen delivery to the patient are well known. Details of these various systems will be hereinafter discussed in detail in the description of the prior art. None of the prior art, however, utilizes sensed hemoglobin saturation to concurrently and adaptively control the $FiO_2$ inspiratory time, and the expiratory end pressure of breathing air from a ventilator supplying pulsed positive pressure breathing air to a patient.

BRIEF DESCRIPTION OF INVENTION

This invention relates to positive pressure ventilation assist respirator systems. The system has particular application in the adaptive control of the inspiratory ventilation time (Tinsp), peak expiratory end pressure (PEEP), and fraction in inspired oxygen ($FiO_2$) and is intended to make more automatic the control of the above patient parameters.

This system utilizes a pulse oximeter to optically determine hemoglobin saturation (HSAT) of the patient's blood, linear interpolate the HSAT to calculate the partial pressure of arterial oxygen ($PaO_2$), and use this information to regulate the length of inspiration time (tinsp), PEEP, and $FiO_2$ to a patient's breathing tube. The control mechanism is derived from the known relationship between the preset level of Tinsp, PEEP, minimum required $FiO_2$ delivered to the patient, and predetermined lung function dynamics in order to maintain a desirable $PaO_2$.

DISCUSSION OF PRIOR ART

The following references represent the closest prior art of which the inventor is aware and is intended to meet the requirements for Information Disclosure Statements.

List of References:

U.S. Pat. No. 2,414,747 Issue Date: Jan. 21, 1947 Inventor: Harry Kirschbaum

U.S. Pat. No. 3,734,091 Issue Date: May 22, 1973 Inventor: Ronald H. Taplin

U.S. Pat. No. 4,326,513 Issue Date: Apr. 27, 1982 Inventor: Volker Schultz et al U.S. Pat. No. 4,889,116 Issue Date: Dec. 26, 1989 Inventor: 4,889,116

U.S. Pat. No. 5,103,814 Issue Date: Apr. 14, 1992 Inventor: Timothy Maher

CONCISE EXPLANATION OF REFERENCES

Devices for controlling the oxygen content of blood by controlling breathing parameters such as inspiratory time, peak expiratory end pressure, and inspired oxygen delivery to a patient are well known. U.S. Pat. No. 2,414,747 issued to Harry Kirschbaum on Jan. 21, 1947 shows a method and apparatus for controlling the oxygen content of the blood of living animals which discloses control of blood oxygen content by the use of an ear oximeter which produces a signal used to control the proportion of inspired oxygen. By directing a beam of light through a capillary bed, as in the ear, the characteristics of the light become modified by the color of the blood that intercepts its path. Thus, the change in oxygen levels of the blood can be detected non-invasively where signals can be generated, amplified and used to control the oxygen supply delivered to a patient. Numerous improvements have been made since that time wherein better matching of oxygen delivery to the needs of the patient have been made such as shown in U.S. Pat. No. 3,734,091 to Ronald H. Taplin issued on May 22, 1973. Taplin discloses an optical oximeter and a temporary oxygen deficient mixture (anoxic) to control blood saturation. Thus, to prevent super saturation, or more than a 100% oxygen saturation, Taplin discloses limiting the oxygen by providing the anoxic mixture each time the saturation of the blood reaches a predetermined percentage level.

An invasive patient data controlled respiration system is shown in U.S. Pat. No. 4,326,513 to Volker Schultz et al issued on Apr. 27, 1982 which shows a patient data controlled respiration system utilizing sensed concentration of oxygen in the patient's blood to control a respirator supplying breathing air having the selected concentration of oxygen to the patient. In such a system, a sensor is connected to the patient for sensing arterial partial pressure of the patient's blood ($PaO_2$). The system further includes a minimizing comparator which has preset threshold levels and determines whether the $FiO_2$ value is above or below those threshold values. When a transient $FiO_2$ value rises above or drops below the threshold value, it causes the control devise to cancel the adjustment to the inspired oxygen and causes the previous amount of oxygen to be supplied to the patient. In this way, there can be only small changes in the original $FiO_2$.

An adaptive oxygen controller utilizing a pulse oximeter for measuring a patient's blood hemoglobin saturation (HSAT) and pulse rate is shown in U.S. Pat. No. 4,889,116 to John C. Taube, issued on Dec. 26, 1989 which shows an oxygen blending system utilizing a patient's sensed hemoglobin saturation to adaptively control the output of an oxygen blender supplying breathing air to the patient. In such a system, the sensed hemoglobin saturation via a pulse oximeter is utilized by the system to adaptively adjust the $FiO_2$ delivered to a breathing mask or hood. In this way, small adjustments in $FiO_2$ minimize the change in a patient's HSAT level.

A self compensating respirator utilizing a pulse oximeter and device for measuring a patient's expired breathing air carbon dioxide ($CO_2$) level is shown in U.S. Pat. No. 5,103,814 to Timothy Maher, issued on Apr. 14, 1992 which shows a respirator system utilizing a patient's sensed HSAT and $CO_2$ to control a ventilator $FiO_2$ and breathing air rate to the patient. In such a system, the sensed HSAT via a pulse oximeter is utilized by the system to periodically decrease the oxygen level delivered to a patient's breathing tube. The system also utilizes sensed $CO_2$ to periodically decrease the rate of the respirator delivering breathing air to the patient. In this way, both $FiO_2$ and rate are systematically decreased lo progressively wean the patient from mechanical ventilation.

The prior art is however, devoid of a system which utilizes sensed hemoglobin saturation to concurrently and adaptively control the FiO₂, inspiratory time, and peak expiratory end pressure of breathing air from a ventilator supplying pulsed positive pressure breathing air to a patient. The adaptive control of FiO₂, inspiratory time, and peak expiratory end pressure is vital for the patient's changing need for increasing and decreasing of blood oxygenation.

OBJECTS OF THE INVENTION

It is therefore an object of the invention to provide a new and useful adaptive control of inspiratory ventilation time, peak expiratory end pressure, and fraction of inspired oxygen.

Another object of the invention is to provide a new and improved respiration system which automatically provides the highest oxygen saturation in the blood while maintaining the highest possible inspiratory ventilation time of oxygen delivered to the patient.

Another object of the invention is to provide a new and improved respiration system which automatically provides the highest oxygen saturation in the blood while maintaining the lowest possible peak expiratory end pressure of oxygen delivered to the patient.

Yet another object of the invention is to provide a new and improved respiration system which automatically provides the highest oxygen saturation in the blood while maintaining the lowest possible fraction of inspired oxygen delivered to the patient.

These and other objects of the invention are achieved by providing an adaptive controller for the adjustment of inspiratory time of oxygen, peak expiratory end pressure of oxygen, and fraction of positive pressure inspired oxygen delivered to a patient. The controller comprises an oximeter connected by an optical sensor to the patient for measuring the patient's blood hemoglobin saturation and pulse rate. The oximeter generates signals representative of the blood hemoglobin saturation and pulse rate. Calculation means are provided which are responsive to the signals from the oximeter for determining the inspiratory time of oxygen, peak expiratory end pressure, and fraction of positive pressure inspired oxygen delivered to the patient. A source of oxygen and a source of air are provided for combining or mixing, and pressurization of the gases and inspiratory administration to the patient. The means for controlling the gas mixture, pressure, and inspiratory administration time is controlled by calculation means to provide a calculated percentage of oxygen, peak expiratory end pressure, and inspiratory time and has an output connected to the patient so that the gas taken in by the patient automatically causes the blood in the patient to reach a predetermined hemoglobin saturation level which adapts to the patient's respiratory requirements.

Other objects and advantages of the present invention will become apparent and obvious from a study of the following description and the accompanying drawings which are merely illustrative of such invention.

DETAILED DESCRIPTION OF THE PREFERRED EMBODIMENT

Figure 1:
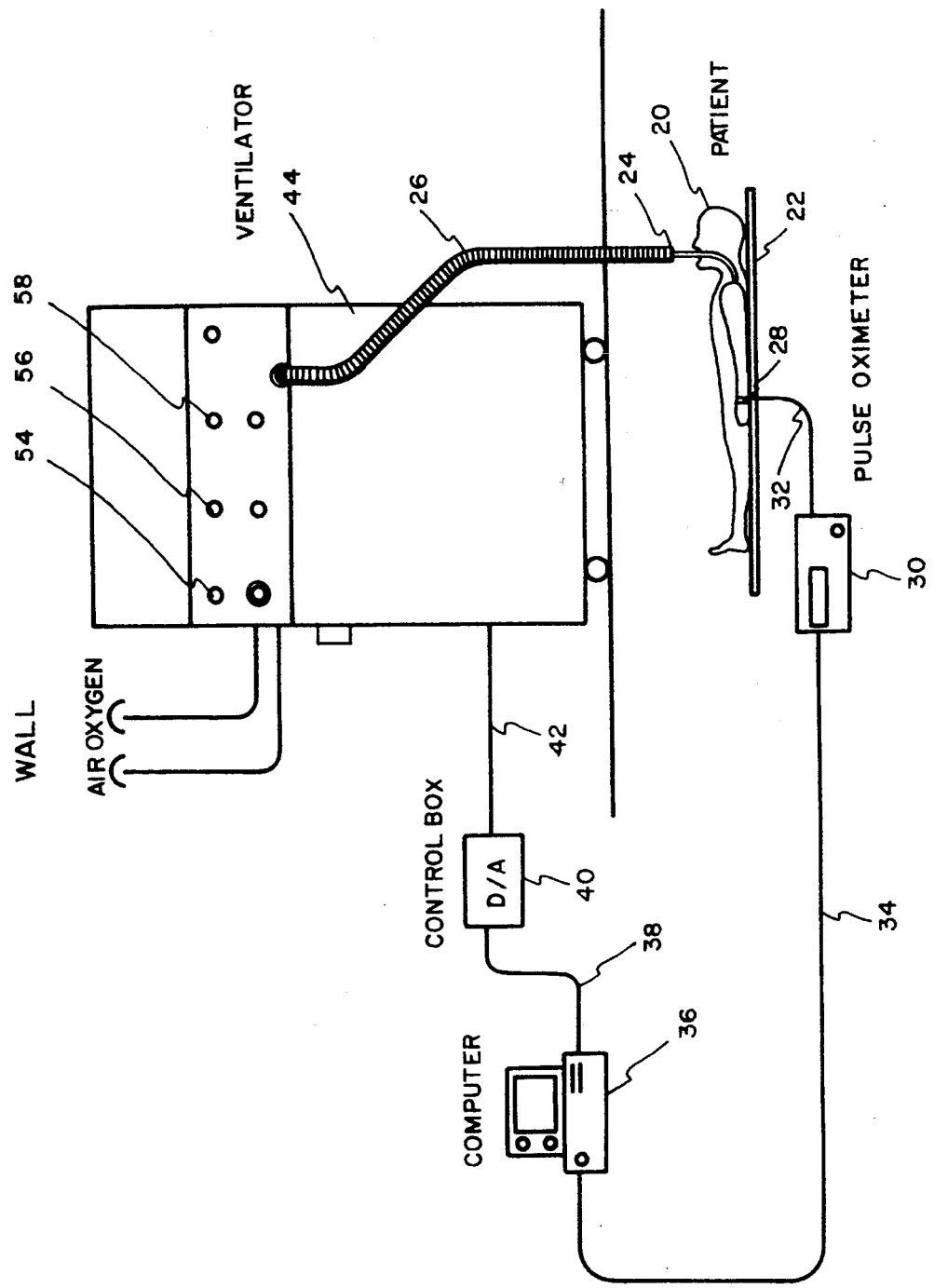
FIG. 1 is diagrammatic view of the automatic ventilator control system of the present invention.

Referring now in greater detail to the various figures of the drawings wherein like reference characters refer to like parts, an automatic controller of ventilator oxygen is shown in FIG. 1 for the purpose of providing positive pressure inspired oxygen with a peak expiratory end pressure and with an inspiratory ventilation time to a patient 20. The patient 20 is shown lying on a mattress 22 having a breathing tube inserted through the mouth and trachea.

The breathing tube controls the breathing environment of the patient and is connected to connective tubing 26 which delivers positive pressure oxygen to the patient.

An optical sensor 28 is placed on the patient's finger. The system also includes a pulse oximeter 30 of the type made by Nellcor Incorporated, of Haywood, Calif. which is shown in U.S. Pat. No. 4,653,498 issued Mar. 31, 1987. Pulse oximeter 30 is connected by a cable 32 to the sensor 28.

The pulse oximeter is connected via a cable 34 to a computer 36. The computer's outputs are connected via cable 38 and then via digital/analog converter 40 and then via lines 42 to a ventilator 44.

Figure 2:
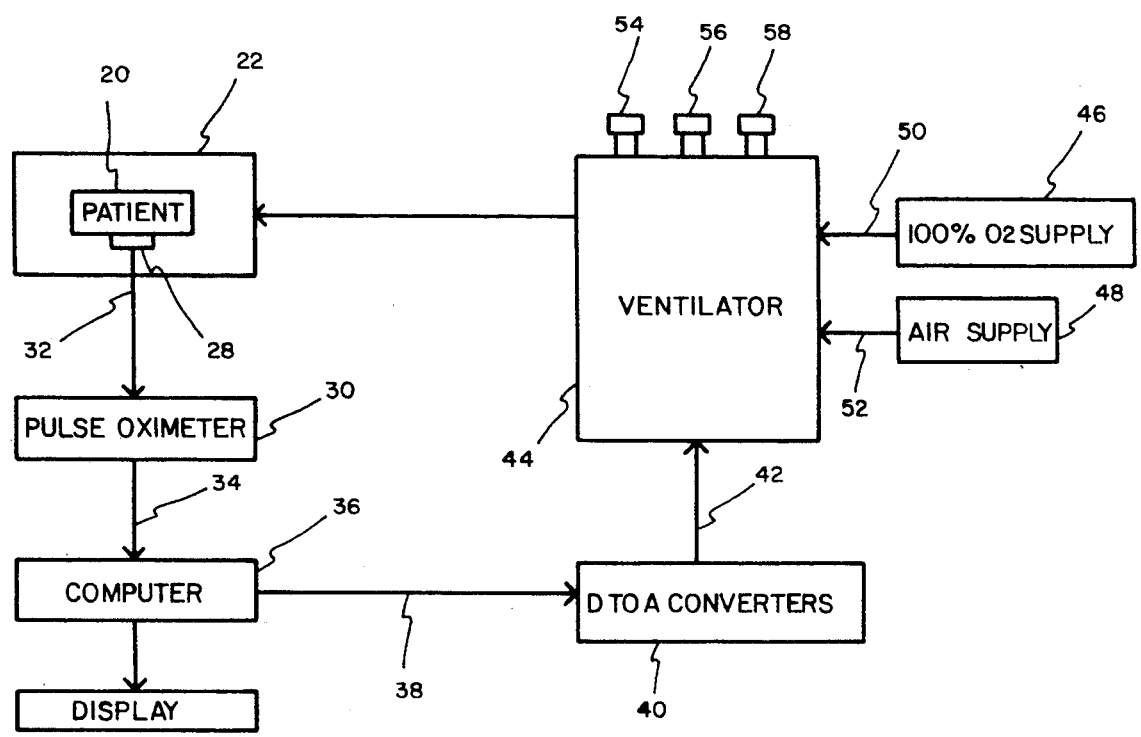
FIG. 2 is a schematic of the diagram of the same.

The connections of the various components of this system are best understood in connection with the schematic block diagram shown in FIG. 2.

As seen in FIG. 2, the sensor 28 is attached to patient 20 and is connected by the cable 32 to pulse oximeter 30. The pulse oximeter 30 determines from the optical sensing of the patient the pulse strength, hemoglobin saturation, and pulse rate. The values of all three of these parameters are digitally displayed on the front of the face of the pulse oximeter in digital form by suitable displays (not shown). The pulse oximeter 30 transfers in digital form over a cable 34 to the computer 36 the digital representations of the pulse strength, hemoglobin saturation (HSAT), and pulse rate. The computer 36 utilizes the hemoglobin saturation which is provided in digital form on lines 34 for determining the partial pressure of arterial oxygen (PaO₂) and thus the appropriate level of inspiratory ventilation time (Tinsp), peak expiratory end pressure (PEEP) of ventilation, and fraction of positive pressure inspired oxygen (FiO₂) to provide to the patient to produce the highest obtainable patient arterial blood oxygen level with a minimum of oxygen necessary to be added to the air supply having a 21% oxygen concentration.

The signals representative of the appropriate Tinsp, PEEP, and FiO₂ are provided in digital form via lines 38 to a digital to analog converter 40. The digital to analog converter provides the signals to the ventilator via lines 42, which controls the inspiratory ventilation time, peak expiratory end pressure of ventilation, and fraction of positive pressure inspired oxygen supplied to the patient. A pure oxygen supply source 45 and air supply 48 containing 21% oxygen concentration are both provided which are connected via tubes 50 and 52, respectively, to the ventilator 44. Conventional solenoid control is used for the purpose of making proportional the Tinsp, PEEP, and FiO₂ in accordance with the signals provided by lines 42 from the digital to analog converter. Accordingly, the appropriate fraction of positive pressure inspired oxygen at an appropriate inspiratory ventilation time and peak expiratory end pressure is provided to the breathing tube 24 via tube 26 to the patient. The ventilator 44 also has attached thereto three manual knobs 54, 55, and 56 which are connected to the oxygen supply solenoid, expiratory resistance solenoid, and the inspiratory time solenoid, respectively. The knobs enable manual regulation by physician or operator to provide an appropriate Tinsp, PEEP, and FiO$_2$ to the patient.

The computer is controlled by program modules to determine Tinsp, PEEP, and FiO$_2$. The flow chart used for determining the roper Tinsp, PEEP and FiO$_2$ to provided to the patient is shown in FIG. 3.

Figure 3:
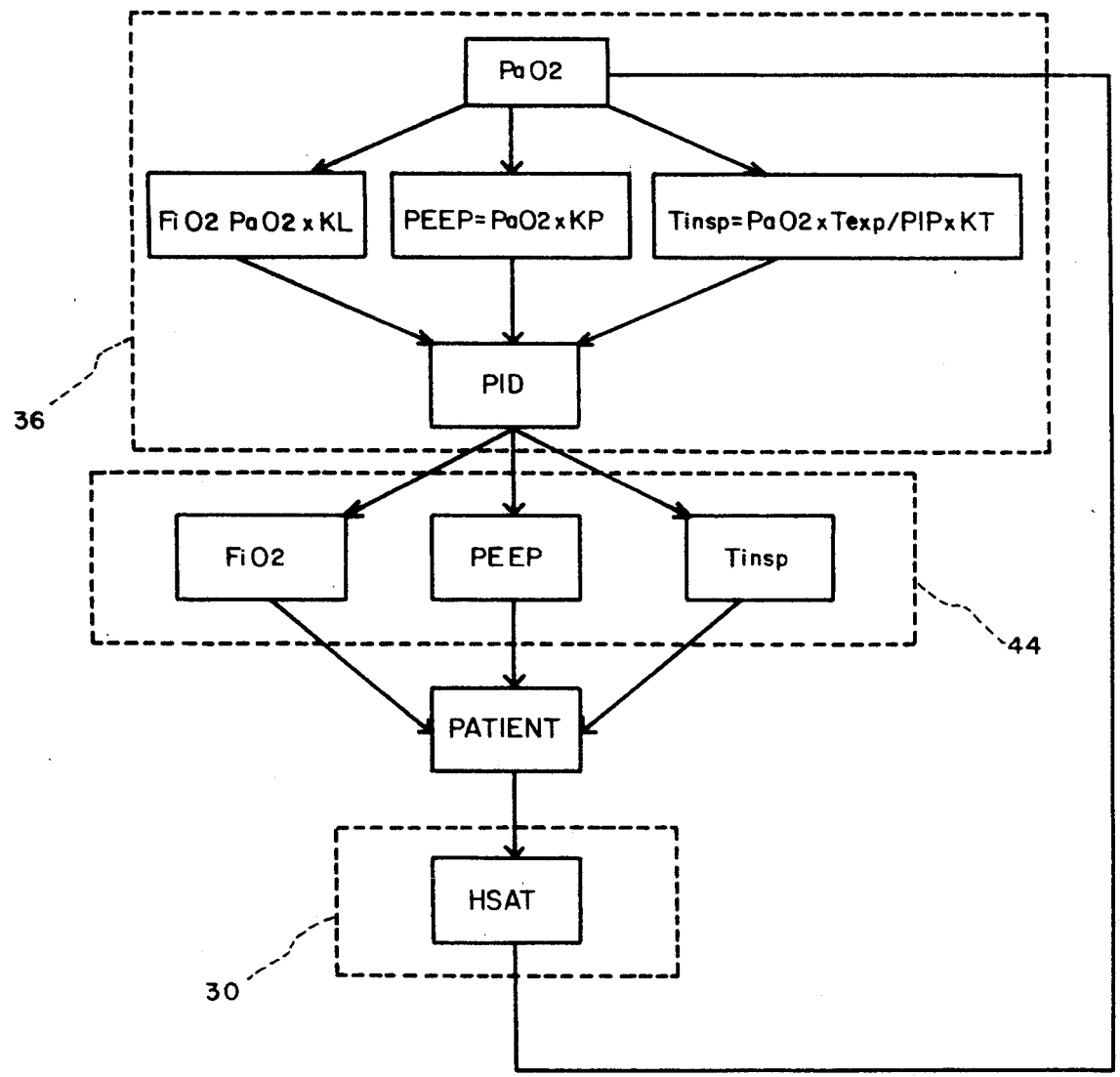
FIG. 3 is a flow diagram showing the operation of the present invention.

Referring to FIG. 3, the TinSD, PEEP, and FiO control program flow diagram is shown. Accordingly, the description of the operation of the Tinsp, PEEP, and FiO$_2$ control program is as follows:

1. The computer receives an HSAT signal from the pulse oximeter and calculates a PaO$_2$ value for the patient.
2. The computer then determines modification values of Tinsp, PEEP, and FiO$_2$ from the calculated PaO$_2$.
3. The computer then determines the proportional, differential, and integral gain coefficients to develop control signals to the ventilator.
4. The computer then sends control signals to the ventilator for the modification of Tinsp, PEEP, and FiO$_2$ values.
5. The patient then breaths in through a breathing tube the positive pressure air at the modified Tinsp, PEEP, and FiO$_2$ values. The values of Tinsp, PEEP, and FiO$_2$ are chosen by the computer to maintain a desired level of the patient's blood oxygen level.
6. The pulse oximeter via an optical sensor connected to the patient calculates the patient's hemoglobin saturation (HSAT). An HSAT signal representing the patient's blood oxygen level is then generated by the pulse oximeter and transmitted to the computer.

In the overall operation of the system, the pulse oximeter and the ventilator 44 as well as the computer 36 are connected as shown in FIG. 1 to the patient. The pulse oximeter 30 is turned on and the patient's hemoglobin saturation (HSAT) is monitored by the attending physician. The positive pressure oxygen percentage (FiO$_2$), peak expiratory end pressure (PEEP), and inspiratory time (Tinsp) are manually controlled by knobs 54, 55, and 56 which are part of manually controlled valves provided on the ventilator 44. The knobs are adjusted until the physician can obtain the highest level of HSAT in the patient's blood level while using the most minimum level of FIO$_2$, minimum level of PEEP, and maximum level of Tinsp for the patient.

The FiO$_2$, PEEP, and Tinsp levels are then controlled automatically by the patient's hemoglobin saturation signals from the pulse oximeter 30.

It can therefore be seen that a new and improved adaptive control system for a fraction of inspared oxygen, peak expiratory end pressure, and inspiratory time has been provided.

The system takes advantage of the unique ability of a pulse oximeter to accurately determine peak arterial oxygen levels. This enables the control system to accurately derive a fraction of inspired oxygen level, peak expiratory end pressure, and inspiratory time which better matches the needs of the patient.

The present invention may, of course, be carried out in other specific ways than those herein set forth without departing from the spirit and essential characteristics of such invention. The present embodiments are, therefore, to be considered in all respects as illustrative and not restrictive, and all changes coming within the meaning and equivalency range of the appended claims are intended to be embraced therein.

What is claimed is:

1. A pulsed positive pressure ventilation assist respirator system comprising:

a ventilator means for providing a selected level of positive pressure respirable gas, said ventilator means further having register means for providing a predetermined level of patient parameters to said ventilator, said patient parameters consisting in inspiration time (T$_{insp}$), positive end expiratory pressure (PEEP) and minimum required fraction inspired oxygen (FiO$_2$);

pulse oximeter means for optically determining the hemoglobin saturation (HSAT) of the patient's blood;

interpolation means for linearly interpolating the HSAT value provided by said pulse oximeter means for calculating the partial pressure of arterial oxygen (PaO$_2$) of a patient;

a control mechanism comprising calculation means for deriving a relationship between said patient parameters in said register means and HSAT value provided by said pulse oximeter means; said control mechanism further comprising adaptive means for providing said register means with updated adjusting values for said patient parameters for maintaining a predetermined PaO$_2$.

* * * * *